(12) United States Patent
Kruglick et al.

(10) Patent No.: US 12,178,751 B2
(45) Date of Patent: Dec. 31, 2024

(54) LASER OPHTHALMIC TREATMENT SYSTEM WITH TIME-GATED IMAGE CAPTURE COMPONENT AND ELECTRONIC DISPLAY

(71) Applicant: LUTRONIC VISION INC., Burlington, MA (US)

(72) Inventors: Ezekiel Kruglick, Poway, CA (US); Mark Meloni, Longmont, CO (US)

(73) Assignee: LUTRONIC VISION INC.

( * ) Notice: Subject to any disclaimer, the term of this patent is extended or adjusted under 35 U.S.C. 154(b) by 1113 days.

(21) Appl. No.: 16/962,889

(22) PCT Filed: Feb. 2, 2018

(86) PCT No.: PCT/US2018/016577
§ 371 (c)(1),
(2) Date: Jul. 17, 2020

(87) PCT Pub. No.: WO2019/152046
PCT Pub. Date: Aug. 8, 2019

(65) Prior Publication Data
US 2021/0045915 A1   Feb. 18, 2021

(51) Int. Cl.
*A61F 9/008*   (2006.01)
*A61B 90/00*   (2016.01)
(Continued)

(52) U.S. Cl.
CPC ............ *A61F 9/008* (2013.01); *A61B 90/361* (2016.02); *A61B 90/37* (2016.02); *H04N 13/239* (2018.05);
(Continued)

(58) Field of Classification Search
CPC ....... A61F 9/008; A61B 90/361; A61B 90/37; A61B 2090/367; A61B 2090/371; H04N 13/239; H04N 23/73
(Continued)

(56) References Cited

U.S. PATENT DOCUMENTS 4,549,787 A * 10/1985 Tanner .................... A61F 9/008
                                                            359/889
4,736,744 A *  4/1988 Koike ................. A61F 9/00821
                                                              606/4

(Continued)

OTHER PUBLICATIONS

"Gear VR (2015) Virtual Reality—SM-R322NZWAXAR," accessed at http://web.archive.org/web/20170814105924/http://www.samsung.com/US/mobile/virtual-reality/gear-vr/gear-vr-sm-r322nzwaxar/, Archived on Aug. 14, 2017, accssed on Dec. 27, 2017, pp. 9.
(Continued)

*Primary Examiner* — Joseph M Dietrich
*Assistant Examiner* — Michael T. Holtzclaw

(57) ABSTRACT

Technologies relate to imaging a treatment area during laser treatment using a time-gated image capture device and an electronic display. During laser treatment, a physician may monitor a treatment area to ensure efficacy and to prevent over-treatment. Light reflected from the area that includes the treatment area may be detected by an image capture component and converted to a signal. An image processor may then generate image data based on the signal and provide the image data to be displayed on an electronic device. A gating component may send instructions to the image capture component and/or the image processor to prevent inclusion of light from one or more laser pulses generated during treatment. Excluding light from the laser pulses may prevent glare in captured images for allowing a monitoring physician to safely and accurately monitor the treatment area.

15 Claims, 8 Drawing Sheets

(51) Int. Cl.
  *H04N 13/239* (2018.01)
  *H04N 23/73* (2023.01)
(52) U.S. Cl.
  CPC ........ *H04N 23/73* (2023.01); *A61B 2090/367* (2016.02); *A61B 2090/371* (2016.02)
(58) Field of Classification Search
  USPC .................................................. 606/4, 1, 2
  See application file for complete search history.

(56) References Cited

U.S. PATENT DOCUMENTS

| | | | |
|---|---|---|---|
| 5,413,555 A | | 5/1995 | McMahan |
| 5,943,117 A | * | 8/1999 | Van de Velde ...... A61B 3/1025 351/205 |
| 5,997,141 A | | 12/1999 | Heacock |
| 2001/0041884 A1 | | 11/2001 | Frey et al. |
| 2009/0093798 A1 | | 4/2009 | Charles |
| 2009/0275929 A1 | * | 11/2009 | Zickler ............... A61F 9/00804 606/4 |
| 2010/0128356 A1 | * | 5/2010 | Feklistov ............. G02B 5/0833 359/637 |
| 2012/0239015 A1 | * | 9/2012 | Liesfeld .................. A61B 3/12 606/4 |
| 2015/0371383 A1 | | 12/2015 | Chanrier et al. |
| 2016/0220416 A1 | | 8/2016 | Adachi |

OTHER PUBLICATIONS

"Ophthalmology," accessed at https://www.baslerweb.com/en/markets/medical-and-life-sciences/ophthalmology/?gclid=CPu4venbr9MCFdSHaAod6fAM2g, accessed on Dec. 27, 2017, pp. 2.

International Search Report and Written Opinion for International Application No. PCT/US2018/016577 mailed on May 15, 2018, pp. 11.

Busck, J. and Heiselberg, H., "Gated viewing and high-accuracy three-dimensional laser radar," Applied Optics, vol. 43, Issue 24, pp. 4705-4710 (Aug. 20, 2004).

Corrasco-Zevallos, O.M., et al., "Live volumetric (4D) visualization and guidance of in vivo human ophthalmic 5 surgery with intraoperative optical coherence tomography," Scientific Reports, vol. 6, Article No. 31689, pp. 1-16 (Aug. 19, 2016).

* cited by examiner

LASER OPHTHALMIC TREATMENT SYSTEM WITH TIME-GATED IMAGE CAPTURE COMPONENT AND ELECTRONIC DISPLAY

CROSS-REFERENCE TO RELATED APPLICATIONS

The present application is a U.S. National Stage filing under 35 U.S.C. § 371 of International Application PCT/US2018/016577, filed Feb. 2, 2018 and entitled "LASER OPHTHALMIC TREATMENT SYSTEM WITH TIME-GATED IMAGE CAPTURE COMPONENT AND ELECTRONIC DISPLAY." The International Application, including any appendices or attachments thereof, is incorporated by reference herein in its entirety.

BACKGROUND

Unless otherwise indicated herein, the materials described in this section are not prior art to the claims in this application and are not admitted to be prior art by inclusion in this section.

During laser treatment, a physician may monitor a treatment area to ensure efficacy and to prevent over-treatment. The physician may monitor the treatment area using a viewing apparatus which may provide light reflected from an area that encompasses the treatment area to be displayed. In order to prevent eye damage or vision loss while monitoring the treatment area, a laser treatment system may include a safety filter to remove light associated with the laser pulses being generated during treatment. The safety filter may allow the physician to monitor the treatment area safely by protecting the physician's eyes from harmful laser pulses.

SUMMARY

The present disclosure generally describes techniques for imaging of a treatment area of an eye undergoing laser treatment.

According to some examples, a method of imaging a treatment area of an eye undergoing laser treatment may comprise directing laser pulses towards the treatment area of the eye, generating image data related to the treatment area by detecting light reflected from an area that includes treatment area, controlling the generation of the image data to exclude light reflected from the area that includes treatment area during a time period in which the laser pulses are incident on the treatment area, and providing the image data to be displayed on an electronic display to present an image of the treatment area during the laser treatment.

According to other examples, an apparatus provided for imaging a treatment area of an eye undergoing laser treatment may comprise a treatment system that may be configured to direct laser pulses towards the treatment area of the eye and an imaging system comprising at least one image capture component. The imaging system may be configured to detect light reflected from an area that includes treatment area, generate image data related to the treatment area based on the light reflected from the area that includes treatment area, and provide the image data to be displayed on an electronic display to present an image of the treatment area during the laser treatment. Generation of the image data may be time-gated to exclude light reflected from the area that includes treatment area during a time period in which the laser pulses directed by the treatment system are incident on the treatment area. The apparatus may also comprise a controller communicatively coupled to the image capture component that may be configured to control performance of operations by the image capture component.

According to further examples, an imaging system for imaging a target area undergoing laser treatment may comprise a lens that may be configured to receive light reflected from the target area in response to laser pulses being directed towards the target area by a laser source communicatively coupled to the imaging system, an image sensor that may be configured to detect and convert the light reflected from the target area to a signal, and an image processor. The image processor may be configured to generate image data based on the signal and provide the image data to be displayed on an electronic display to present an image of the target area during the laser treatment. The imaging system may further comprise a gating component that may be configured to control a time-gating of the imaging system such that the image data excludes light reflected from the target area during a time period in which the laser pulses directed by the laser source are incident on the target area.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1:
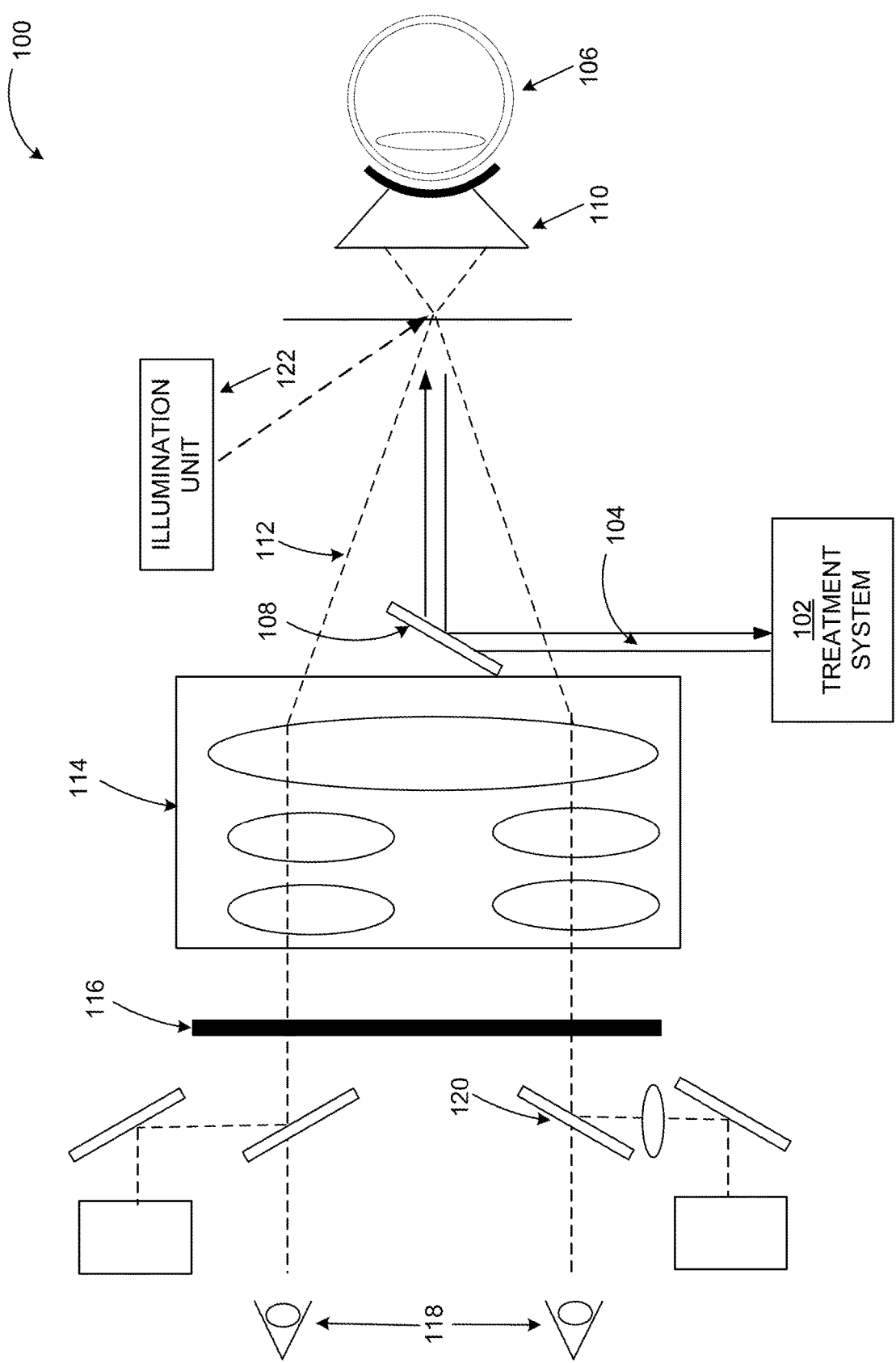
FIG. 1 includes a conceptual illustration of an example laser ophthalmic treatment system.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. The aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to methods, apparatus, systems, devices, and/or computer program products related to imaging a treatment area in an eye undergoing laser treatment using a time-gated image capture component and electronic display.

Briefly stated, technologies are generally described to image a treatment area during laser treatment using a time-gated image capture device and an electronic display. During laser treatment, a physician may monitor a treatment area to ensure efficacy and to prevent over-treatment. Light reflected from the area that includes treatment area may be detected by an image capture component and converted to a signal. An image processor may then generate image data based on the signal and provide the image data to be displayed on an electronic device. A gating component may send instructions to the image capture component and/or the image processor to prevent inclusion of light from one or more laser pulses generated during treatment. Excluding light from the laser pulses may prevent glare in captured images allow a monitoring physician to safely and accurately monitor the treatment area.

FIG. 1 includes a conceptual illustration of an example laser ophthalmic treatment system, arranged in accordance with at least some embodiments described herein.

As shown in diagram 100, a treatment system 102 may direct one or more laser pulses 104 toward a treatment area of an eye 106. The treatment system 102 may include components such as a laser source, a laser controller, a detector, and an illumination component for example. The laser pulses 104 may be directed toward the treatment area of the eye 106 by one or more dichroic mirrors 108 along the optical path of the laser pulses 104. A contact lens 110 may be utilized on the surface of the eye 106 to further direct the laser pulses 104 toward the treatment area in the eye 106.

The treatment area may be illuminated by an illumination unit 122 during laser treatment to allow for the treatment area to be monitored during at least a portion of the treatment. Light 112 reflected from the treatment area may be directed toward a series of lenses 114, and the series of lenses 114 may focus the light 112 reflected from the treatment area toward a safety filter 116. As used herein "light reflected from the treatment area" refers to light reflected from an area of the treated organ (e.g., the eye), where the area encompasses the treatment area. For example, a laser pulse may illuminate a spot on the retina and "the reflected light" may be reflected from the area illuminated by the laser spot as well as the additional regions of the retina surrounding the laser spot. The safety filter 116 may filter light corresponding with the laser pulses 104 from the light 112 reflected from the treatment area. The filtered light 112 may then be directed toward a viewing apparatus 118 by dichroic mirrors 120 to allow a physician to monitor the treatment area during laser treatment. The viewing apparatus may include a camera or similar image capture device or it may also include the eyes of a doctor or other healthcare professional administering the laser treatment. In an example scenario, the laser pulses 104 may have a wavelength of 527 nm which may be used to damage the target tissue but may also be capable of damaging healthy tissue as well. The safety filter 116 may be designed to exclude light with a wavelength of 527 nm in order to protect a physician from the potentially damaging light when monitoring the treatment area using the viewing apparatus 118. The physician may monitor the treatment area during laser treatment to ensure efficacy of the laser treatment or to ensure healthy tissue is not damaged.

Figure 2:
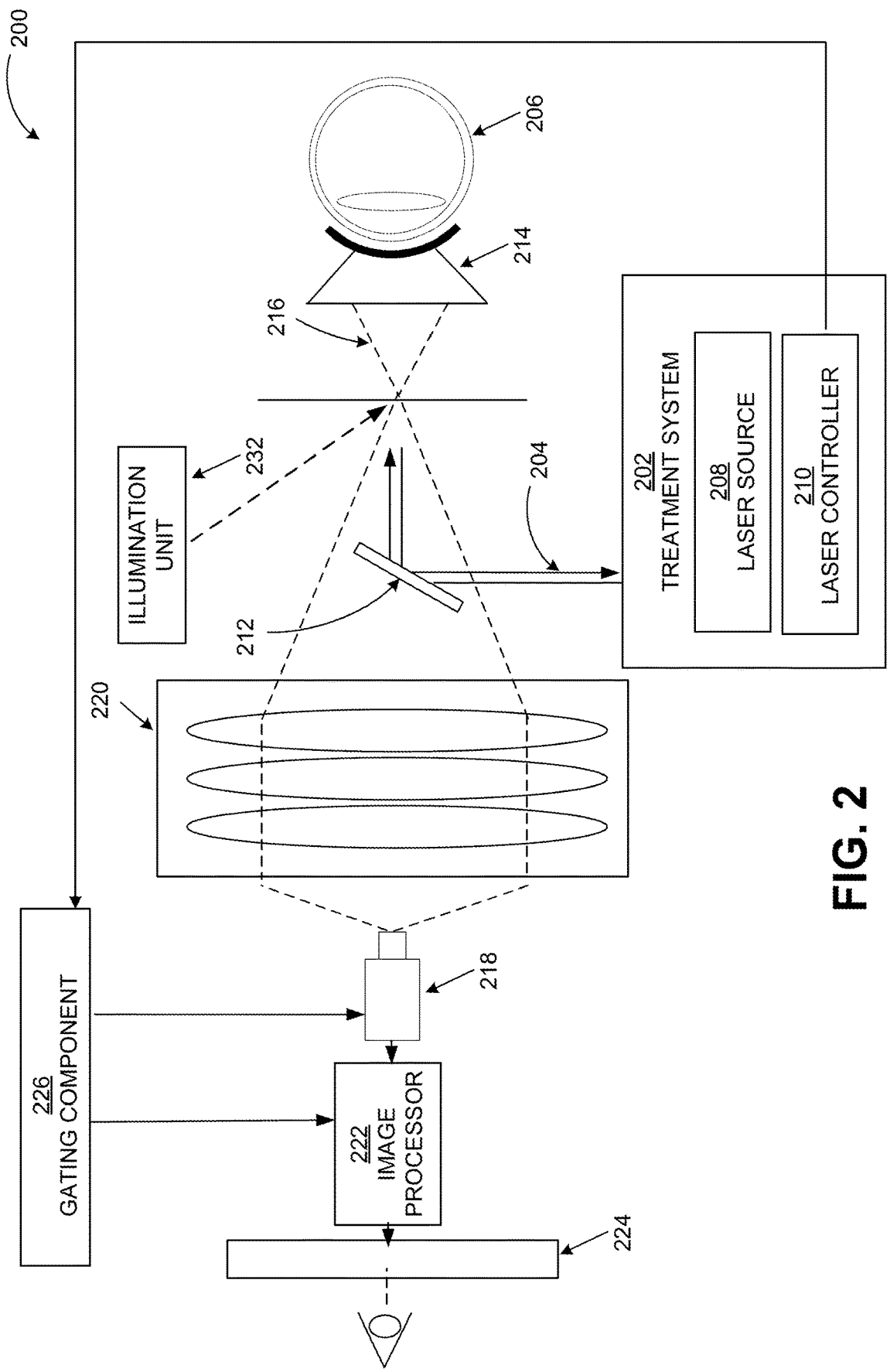
FIG. 2 includes a conceptual illustration of an example system to image a treatment area of an eye undergoing laser treatment that includes a single time-gated image capture component and electronic display.

Throughout the lifecycle of the treatment system 102, the safety filter 116 may degrade and may need to be replaced in order to ensure protection of physicians that may monitor the treatment area using the viewing apparatus 118. Additionally, the safety filter 116 may fail unexpectedly while the physician is monitoring the treatment area during laser treatment. Failure of the safety filter 116 may cause the physician to be exposed to light from the laser pulses 104 which may cause eye damage or vision loss. As shown in FIG. 2 and according to some embodiments described herein, the safety filter 116 may be replaced with a time-gated image capture component to capture image data associated with the treatment area. In some examples, the image data may then be displayed on an electronic display to allow an attending physician to monitor the treatment area during laser treatment. Such embodiments may reduce the risk for the attending physician suffering eye damage or vision loss in the event of the safety filter 116 failing. Additionally, replacing the safety filter 116 with a time-gated image capture device may reduce repair costs during the life-cycle of the treatment system 102.

FIG. 2 includes a conceptual illustration of an example system to image a treatment area of an eye undergoing laser treatment that includes a single time-gated image capture component and electronic display, arranged in accordance with at least some embodiments described herein.

As shown in diagram 200, a treatment system 202 may direct a laser pulse 204 toward a treatment area of an eye 206. The treatment system 202 may include components such as a laser source 208, a laser controller 210, a white LED to illuminate the treatment area, or an additional illumination unit 232 for example. The laser source 208 may include a semiconductor laser diode, a super-luminescent laser diode, a chemical laser, a gas laser, a solid-state laser, or an optical fiber diode, for example. The laser controller 210 may instruct the laser source 208 to direct the laser pulse 204 to the treatment area of the eye 206. The laser pulse 204 may be directed toward the treatment area of the eye 206 by one or more dichroic mirrors 212 along the optical path of the laser pulse 204. A contact lens 214 may be utilized on the surface of the eye 206 to further direct the laser pulses 204 toward the treatment area in the eye 206.

During at least a portion of the laser treatment, light 216 reflected from the area that includes the treatment area may be detected by an image capture device 218. The image capture device 218 may include a charged coupled device (CCD), a complementary metal-oxide-semiconductor (CMOS), or a N-type metal-oxide-semiconductor (NMOS). The image capture device 218 may be capable of detecting light in one or more spectral ranges which may include a visible light range, an ultra-violet (UV) light range, an infrared (IR) light range, and/or a sub-spectral range. The image capture device 218 may have a distinct light level setting to capture light of a particular wavelength or intensity. In some embodiments, the image capture device 218 may include an optical shutter component. In the example, the light 216 reflected from the area that includes treatment area may be focused and directed to the image capture device 218 for detection by a series of lenses 220 (which may be simplified, over the lenses shown conceptually, in situations where 218 is a single imager). The image capture subs-system of a laser treatment system according to embodiments may be implemented in a variety of configurations.

The image capture device 218 may then convert the detected light to a signal and transmit the signal to an image processor 222. The image processor 222 may include a computing device such as a server, a desktop computer, a mobile computer, a special purpose computing device, or a component level processor, for example. The image processor 222 may generate image data based on the signal, and provide the image data to be displayed on an electronic display 224. The image processor 222 may perform operations to enhance the image data such as edge filtering, edge detection, area agglomeration, contrast adjustment, or overlaying the image data to highlight changes in the treatment area among other techniques. Image data may include single-shot images, one or more captured images arranged in sequence, or a video stream composed from the captured images. The electronic display 224 may be integrated with the treatment system 202, integrated with the image capture device 218, or may include a separate device such as a computer monitor, a television, a projector, a mobile device, or a stereoscopic display device for example. The electronic display 224 may include one or more user interface components such as a menu, control elements or overlay elements that an attending physician may utilize the displayed image data to monitor the treatment area during laser treatment. The electronic display 224 may be proximate or distant from the image capture device 218.

In order to prevent light from the laser pulse 204 from being displayed on the electronic display 224, the laser controller 210 may provide the timing of the laser pulse 204 to a gating component 226, and the gating component 226 may determine a time period the laser pulse 204 is incident with the treatment area. The gating component 226 may determine the time period by determining the timing of laser pulses directed toward the treatment area, determining the duration of the laser pulses, and/or determining a time interval between the laser pulses. The gating component 226 may also determine the time period by determining an intensity associated with the light 216 reflected from the area that includes treatment area, inferring the laser pulse 204 is incident on the treatment area based on the intensity being above a particular threshold, and determining the time period based on the duration the intensity is above the threshold. The gating component 226 may transmit instructions based on the time period in which the laser pulse 204 is incident on the treatment area of the eye 206 to the image capture device 218 and/or the image processor 222.

For example, the gating component 226 may instruct the image capture device 218 to cease detection during the time period that the laser pulses 204 are incident on the treatment area. Alternatively, the gating component 226 may instruct the image processor 222 to exclude light detected during the time period from the generated image data or may instruct the image processor 222 to exclude image data from the time period when providing the image data for display. In some examples, the gating component 226 may instruct the image capture device 218 to close the optical shutter during the time period. In an example scenario, during laser treatment, the laser controller 210 may direct a laser pulse 204 to the treatment area of the eye 206 and may provide the timing of the laser pulse 204 to the gating component 226. The gating component 226 may then instruct the image capture device 218 to temporarily cease detection of light from the area that includes treatment area of the eye 206 while the laser pulse 204 is incident to the treatment area.

In some examples, light reflected from the area that includes treatment area may be detected by a first image capture device and a second image capture device during at least a portion of the laser treatment. The image capture devices may each include a camera capable of detecting light in one or more spectral ranges which may include a visible light range, an ultra-violet (UV) light range, an infrared (IR) light range, and/or a sub-spectral range. The image capture devices may include a charged coupled device (CCD), a complementary metal-oxide-semiconductor (CMOS), or a N-type metal-oxide-semiconductor (NMOS). The image capture devices may each have a distinct light level setting to capture light of a particular wavelength or intensity and may include an optical shutter component. In one example, the light reflected from the area that includes treatment area may be focused and directed to the first image capture device and the second image capture device by a series of lenses.

Figure 3:
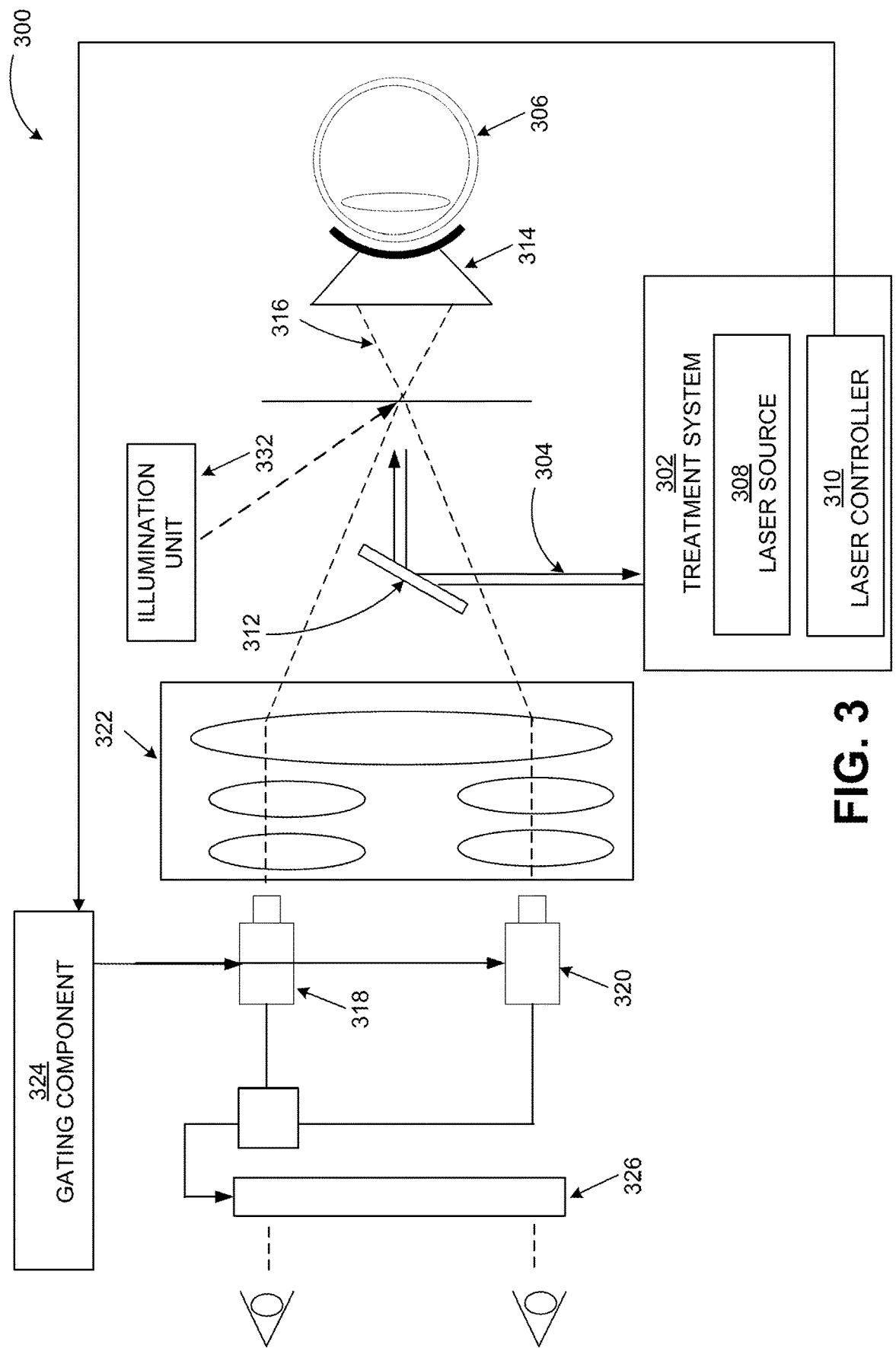
FIG. 3 includes a conceptual illustration of an example system to image a treatment area of an eye undergoing laser treatment that includes at least two time-gated image capture components and electronic display to enable presentation of a stereoscopic image.

FIG. 3 includes a conceptual illustration of an example system to image a treatment area of an eye undergoing laser treatment that includes at least two time-gated image capture components and electronic display to enable presentation of a stereoscopic image, arranged in accordance with at least some embodiments described herein.

As shown in diagram 300, a treatment system 302 may direct a laser pulse 304 toward a treatment area of an eye 306. The treatment system 302 may include components such as a laser source 308 and a laser controller 310. A separate illumination unit 332 may illuminate the treatment area. The laser controller 310 may instruct the laser source 308 to direct the laser pulse 304 to the treatment area of the eye 306. The laser pulse 304 may be further directed toward the treatment area of the eye 306 by one or more dichroic mirrors 312 along the optical path of the laser pulse 304. A contact lens 314 may be utilized on the surface of the eye 306 to further direct the laser pulse 304 toward the treatment area in the eye 306.

The first image capture device 318 and the second image capture device 320 may detect light 316 from the area that includes treatment area and convert the detected light to a first signal and a second signal to transmit to an image processor. The image processor may be a computing device such as a server, a desktop computer, a mobile computer, a special purpose computing device, or a component level processor, for example. The image processor may then generate a first set of image data and a second set of image data based on the first signal and the second signal, respectively. The image processor may perform operations to enhance the image data such as filtering, edge detection, area agglomeration, contrast adjustment, or overlaying the set of image data to highlight changes in the treatment area, among other techniques.

The gating component 324 may transmit the instructions to the first image capture device 318, the second image capture device 320, and the image processor based on a time period the laser pulse 304 is incident on the treatment area.

The gating component 324 may determine the time period by determining the timing of laser pulses directed toward the treatment area, determining the duration of the laser pulses, and/or determining a time interval between the laser pulses. The gating component 324 may determine the time period by determining an intensity associated with the light 316 reflected from the area that includes treatment area, inferring the laser pulse 304 is incident on the treatment area based on the intensity being above a particular threshold, and determining the time period based on the duration the intensity is above the threshold.

The gating component 324 may then transmit instructions to the first image capture device 318 and the second image capture device 320 which may include instructions to cease detection during the time period that the laser pulse 304 is incident on the treatment area. The gating component 324 may instruct the image processor to exclude light detected during the time period that the laser pulse 304 is incident on the treatment area from the first set of image data and the second set of image data. The gating component 324 may also instruct the image processor to exclude image data associated with the time period the laser pulse 304 is incident on the treatment area from each set of image data. In some examples, the gating component 324 may instruct the first image capture device 318 and the second image capture device 320 to close an optical shutter during the time period to prevent detection of the laser pulse 304.

The image processor may provide the first set of image data and the second set of image data to an electronic display 326 to present a stereoscopic image of the treatment area during the laser treatment. The electronic display 326 may be integrated with the treatment system 302, integrated with the image capture devices, or may be a separate display device such as a virtual reality headset. The electronic display 326 may include a user interface with components such as menus, control elements, or overlay elements to enable interaction with the image data. The electronic display 326 may be stereoscopic. The electronic display 326 may include lenses, eye cups, head mounting, or other forms of image presentation.

For example, during laser treatment, the first image capture devices 318 and the second image capture device 320 may continuously detect light 316 from the area that includes treatment area and convert the detected light to a corresponding signal. The image processor may then generate the first set of image data and the second set of image data based on the respective signals. The laser controller 310 may direct a laser pulse toward the treatment area and send the timing of the laser pulse to the gating component 324. The gating component 324 may send instructions to the image processor to exclude image data generated during the time period the laser pulse was incident with the treatment area from the first set of image data and the second set of image data. The image processor may then provide the first set of image data and the second set of image data to an electronic display 326 with the image data associated with the time period removed. The electronic display 326 may be a virtual reality headset intended to provide the attending physician with a stereoscopic view of the treatment area. The attending physician may monitor the treatment area using the image data displayed on the virtual reality headset to ensure efficacy of the treatment and prevent damage to healthy tissue.

The depiction of the series of lenses 114, 220, and 322 in FIGS. 1, 2, and 3, respectively, includes example configurations for illustration purposes only, and is not intended to impose a limitation on embodiments. For example, stereoscopic imaging with dual cameras, where each camera is directed to a different spectrum or to the same spectrum may be used. Other imaging approaches using single camera, as well as, single or multiple spectra may also be implemented using the principles described herein.

Figure 4:
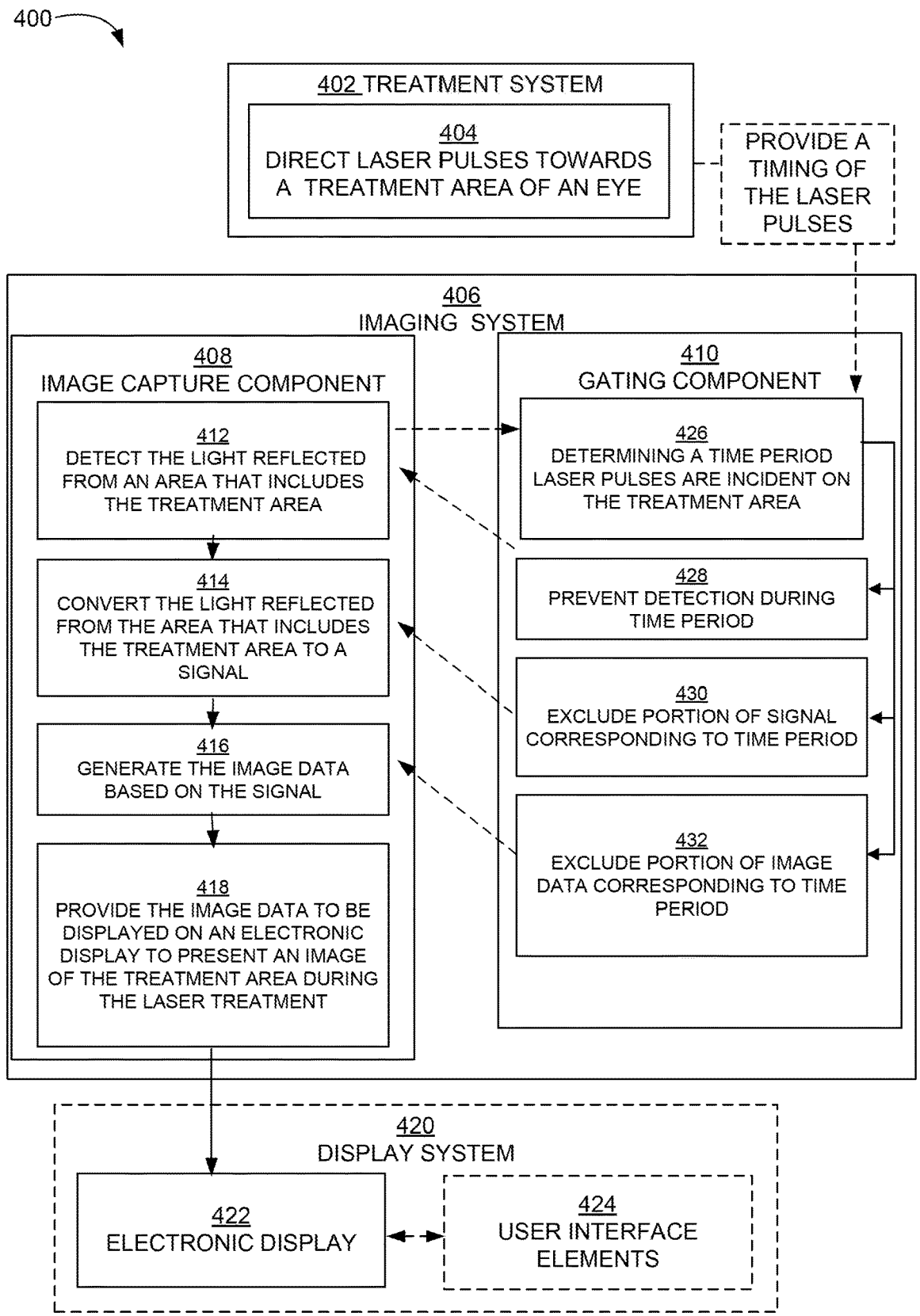
FIG. 4 illustrates an iterative flow process for imaging of a treatment area of an eye undergoing laser treatment.

FIG. 4 illustrates an example interaction between various systems for imaging a treatment area of an eye undergoing laser treatment and providing the image for display in near real-time, arranged in accordance with at least some embodiments described herein.

As shown in diagram 400, a treatment system 402 begin a laser treatment session by performing the operation 404, where one or more laser pulses may be directed toward a treatment area in an eye. The treatment system 402 may provide the timing of the one or more laser pulses to an imaging system 406. The imaging system 406 may include an image capture component 408 and a gating component 410. The image capture component 408 may include an image capture device and an image processor for example.

The image capture component 408 may perform the operation 412, where light reflected from the area that includes treatment area is detected. The image capture component 408 may then perform operation 414, where the detected light from the area that includes treatment area is converted to a signal. Operation 414 may be followed by operation 416, where an image processor may generate image data based on the signal. The image processor may the perform operation 418, where the image data may be provided to the display system 420 to be displayed on the electronic display 422. The electronic display 422 may include a computer monitor, a television, a projector, a mobile device, or a stereoscopic display device for example. An attending physician may interact with the image data displayed on the electronic display 422 using one or more user interface elements 424 such as menus, control elements, or overlay elements.

The gating component 410 may transmit instructions to the image capture component 408 in order to prevent light from the one or more laser pulses from being included in the image data displayed on the electronic display 422. The gating component 410 may perform the operation 426, where a time period the one or more laser pulses are incident on the treatment area is determined based on the timing of the laser pulses received from the treatment system 402. The gating component 410 may determine the time period the laser pulses are incident on the treatment area by determining the timing of laser pulses directed toward the treatment area, determining the duration of the laser pulses, and/or determining a time interval between the laser pulses. The gating component 410 may also determine the time period by determining an intensity associated with the light reflected from the area that includes treatment area, inferring the laser pulses are incident on the treatment area based on the intensity being above a particular threshold, and determining the time period based on the duration the intensity is above the threshold.

Based on the determined time period, the gating component 410 may perform the operation 428, where the gating component 410 may transmit instructions to cease detection during the time period the one or more laser pulses are incident on treatment area to the image capture component 408. The image capture component 408 may perform the operation 412 based on the instructions received from the gating component 410. Alternatively, the gating component 410 may perform the operation 430 after operation 426, where the gating component 410 may transmit instructions to the image processor to exclude light detected during the determined time period from the signal. The image capture component 408 may receive the instructions and exclude light detected during the time period from the signal when performing operation 412.

The gating component 410 may also perform operation 432, where the gating component 410 may transmit instructions to the image processor to exclude a portion of image data corresponding to the time period determined in operation 426. Upon receiving the instructions, the image capture component 408 may exclude image data corresponding to the time period the one or more laser pulses when generating the image data in operation 414. The gating component 410 may perform one or more of the operations 428, 430, and 432 to prevent glare from the one or more laser pulses from being displayed on the electronic display 422.

Figure 5:
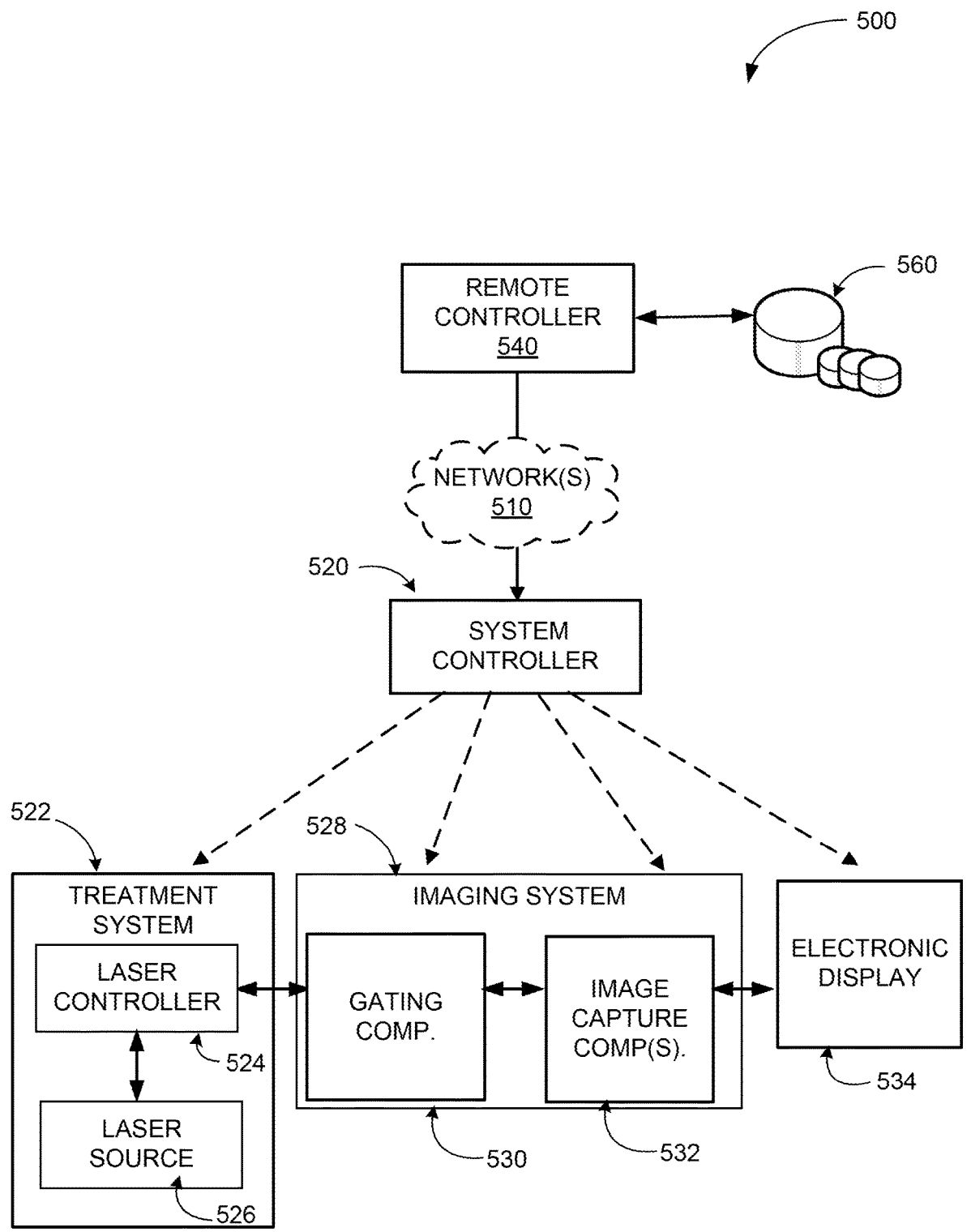
FIG. 5 illustrates major components of an example system configured to image a treatment area of an eye undergoing laser treatment.

FIG. 5 illustrates major components of an example system configured to image a treatment area of an eye undergoing laser treatment, arranged in accordance with at least some embodiments described herein.

As shown in diagram 500, a treatment system 522, the imaging system 528 and the electronic display 534 may be governed by the system controller 520. The system controller 520 may be managed manually through a variety of inputs, may operate automatically after receiving one or more instructions, or may be operated independently by software. The system controller 520 may also be partially or entirely managed by a remote controller 540, for example, via network 510. The remote controller 540 may be managed manually through a variety of inputs, may operate automatically after receiving one or more instructions, or may be operated independently by software. Data associated with imaging a treatment area in an eye undergoing laser treatment with a time-gated image capture component and electronic display may be stored at and/or received from data stores 560.

The treatment system 522 may include a laser controller 524 and a laser source 526. The laser source 526 may include a semiconductor laser diode, a super-luminescent laser diode, a chemical laser, a gas laser, a solid-state laser, or an optical fiber diode, for example. The laser controller 524 may direct one or more laser pulses to a treatment area in an eye undergoing laser treatment via the laser source 526. The laser controller 524 may also transmit the timing of the one or more laser pulses such as a time period the one or more laser pulses are incident on the treatment area in the eye to the imaging system 528.

The imaging system 528 may include a gating component 530 and one or more image capture components 532. The one or more image capture devices 532 may detect light reflected from the area that includes treatment area during laser treatment and convert the detected light to a signal. An image processor may then generate image data based on the signal and provide the image data to be displayed on the electronic display 534. The electronic display 534 may include a computer monitor, a television, a projector, a mobile device, or a stereoscopic display device for example.

The gating component 530 of the imaging system 528 may transmit instructions to the one or more image capture devices 532 based on the timing of the one or more laser pulses received from the laser controller 524. The gating component 530 may determine a time period that the one or more laser pulses are incident on the treatment area by determining the timing of laser pulses directed toward the treatment area, determining the duration of the laser pulses, and/or determining a time interval between the laser pulses. The gating component 530 may also determine the time period by determining an intensity associated with the light reflected from the area that includes treatment area, inferring the laser pulses are incident on the treatment area based on the intensity being above a particular threshold, and determining the time period based on the duration the intensity is above the threshold.

The instructions transmitted by the gating component 530 may be intended to prevent detection of light from the one or more laser pulses during laser treatment. For example, the gating component 530 may instruct the one or more image capture devices 532 to cease detection during the time period that the laser pulses are incident on the treatment area. Alternatively, the gating component 530 may instruct the image processor to exclude light detected during the time period from the generated image data or may instruct the image processor to exclude image data from the time period when providing the image data for display. In some examples, the one or more image capture devices 532 may include an optical shutter, and the gating component 530 may transmit instructions to close the optical shutter during the time period.

Figure 6:
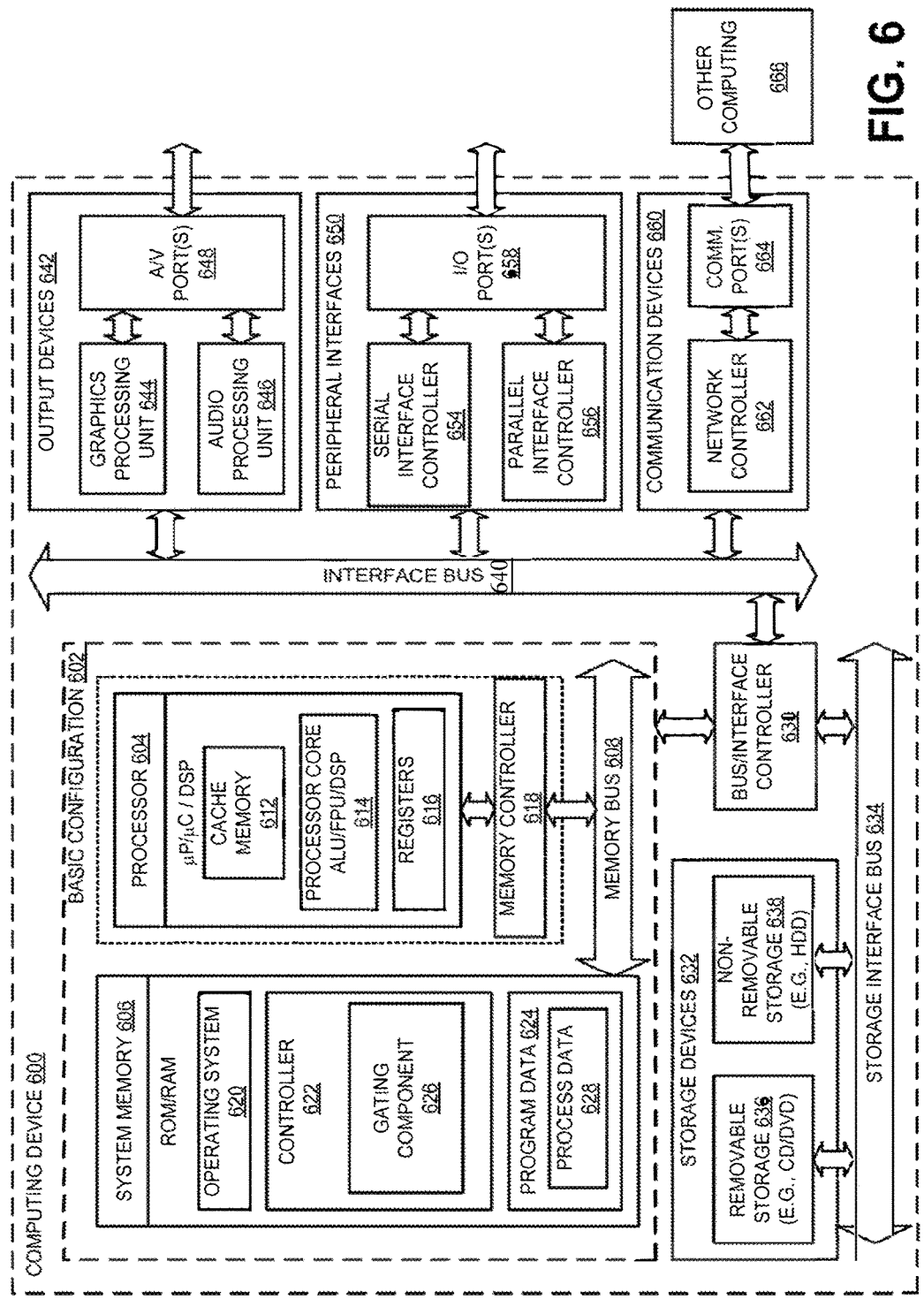
FIG. 6 illustrates a computing device, which may be communicatively coupled to an apparatus or system configured to image a treatment area of an eye undergoing laser treatment.

FIG. 6 illustrates a computing device, which may be communicatively coupled to an apparatus or system configured to image a treatment area of an eye undergoing laser treatment, arranged in accordance with at least some embodiments described herein.

In an example basic configuration 602, the computing device 600 may include one or more processors 604 and a system memory 606. A memory bus 608 may be used to communicate between the processor 604 and the system memory 606. The basic configuration 602 is illustrated in FIG. 6 by those components within the inner dashed line.

Depending on the desired configuration, the processor 604 may be of any type, including but not limited to a microprocessor ($\mu P$), a microcontroller ($\mu C$), a digital signal processor (DSP), or any combination thereof. The processor 604 may include one or more levels of caching, such as a cache memory 612, a processor core 614, and registers 616. The example processor core 614 may include an arithmetic logic unit (ALU), a floating point unit (FPU), a digital signal processing core (DSP Core), or any combination thereof. An example memory controller 618 may also be used with the processor 604, or in some implementations, the memory controller 618 may be an internal part of the processor 604.

Depending on the desired configuration, the system memory 606 may be of any type including but not limited to volatile memory (such as RAM), non-volatile memory (such as ROM, flash memory, etc.) or any combination thereof. The system memory 606 may include an operating system 620, a controller 622, and program data 624. The controller 622 may include a gating component 626. The gating component 626 may transmit instructions to one or more image capture devices or an image processor to exclude light from one or more laser pulses from being displayed. The gating component 626 may transmit the instructions based on a determined time period that one or more laser pulses are incident on the treatment area. Program data 624 may include process data 628. The process data 628 may include data associated with imaging a treatment area in an eye undergoing laser treatment with a time-gated image capture component and electronic display.

The computing device 600 may have additional features or functionality, and additional interfaces to facilitate communications between the basic configuration 602 and any desired devices and interfaces. For example, a bus/interface controller 630 may be used to facilitate communications between the basic configuration 602 and one or more data storage devices 632 via a storage interface bus 634. The data storage devices 632 may be one or more removable storage devices 636, one or more non-removable storage devices 638, or a combination thereof. Examples of the removable storage and the non-removable storage devices include magnetic disk devices such as flexible disk drives and hard-disk drives (HDDs), optical disk drives such as compact disc (CD) drives or digital versatile disk (DVD) drives, solid state drives (SSDs), and tape drives to name a few. Example computer storage media may include volatile and nonvolatile, removable and non-removable media implemented in any method or technology for storage of information, such as computer readable instructions, data structures, program modules, or other data.

The system memory 606, the removable storage devices 636 and the non-removable storage devices 638 are examples of computer storage media. Computer storage media includes, but is not limited to, RAM, ROM, EEPROM, flash memory or other memory technology, CD-ROM, digital versatile disks (DVDs), solid state drives (SSDs), or other optical storage, magnetic cassettes, magnetic tape, magnetic disk storage or other magnetic storage devices, or any other medium which may be used to store the desired information and which may be accessed by the computing device 600. Any such computer storage media may be part of the computing device 600.

The computing device 600 may also include an interface bus 640 for facilitating communication from various interface devices (e.g., one or more output devices 642, one or more peripheral interfaces 650, and one or more communication devices 660) to the basic configuration 602 via the bus/interface controller 630. Some of the example output devices 642 include a graphics processing unit 644 and an audio processing unit 646, which may be configured to communicate to various external devices such as a display or speakers via one or more A/V ports 648. One or more example peripheral interfaces 650 may include a serial interface controller 654 or a parallel interface controller 656, which may be configured to communicate with external devices such as input devices (e.g., keyboard, mouse, pen, voice input device, touch input device, etc.) or other peripheral devices (e.g., printer, scanner, etc.) via one or more I/O ports 658. An example communication device 660 includes a network controller 662, which may be arranged to facilitate communications with one or more other computing devices 666 over a network communication link via one or more communication ports 664. The one or more other computing devices 666 may include servers at a datacenter, customer equipment, and comparable devices.

The network communication link may be one example of a communication media. Communication media may be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

The computing device 600 may be implemented as a part of a general purpose or specialized server, mainframe, or similar computer that includes any of the above functions. The computing device 600 may also be implemented as a personal computer including both laptop computer and non-laptop computer configurations.

Figure 7:
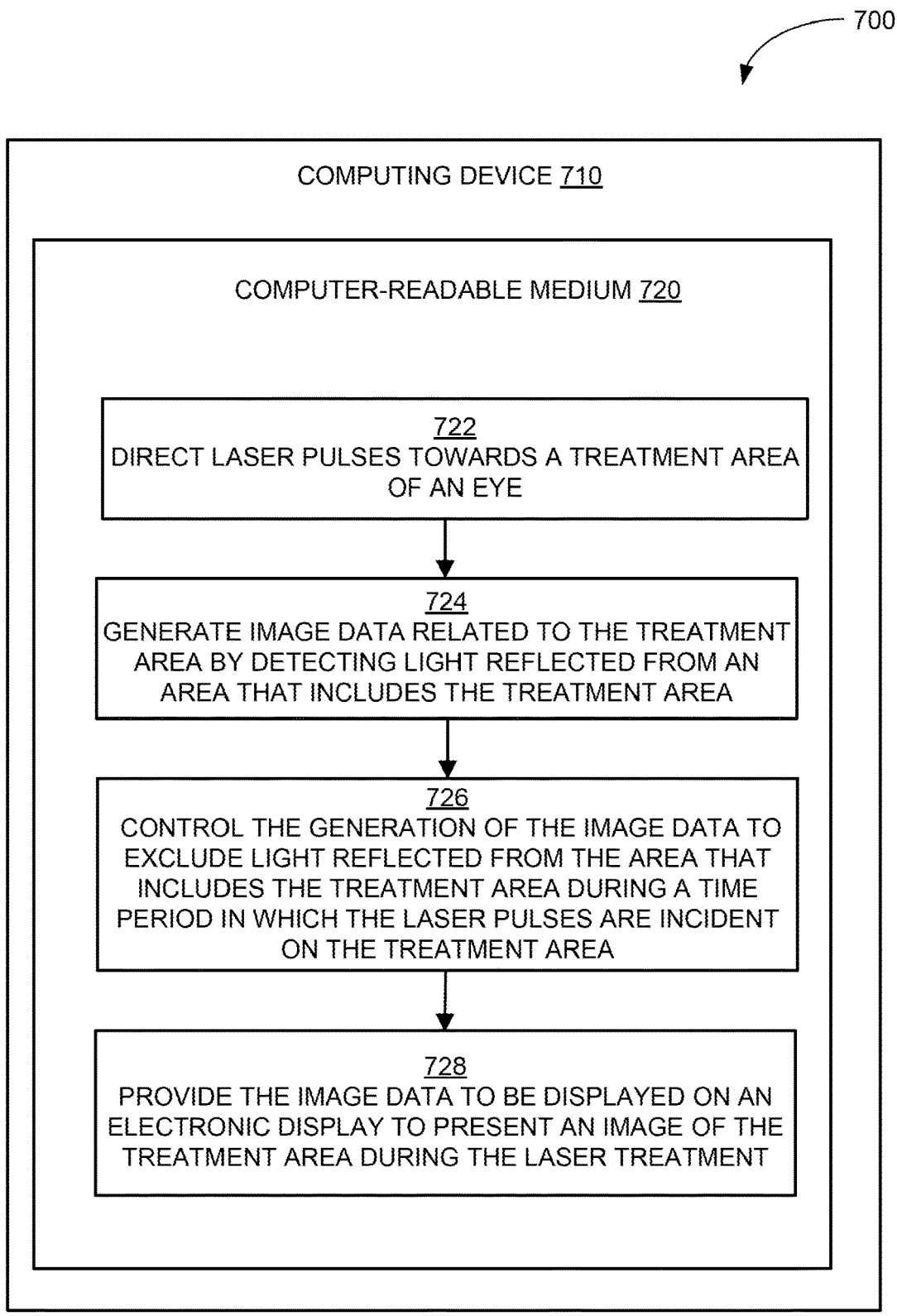
FIG. 7 is a flow diagram illustrating an example method to image a treatment area of an eye undergoing laser treatment that may be performed by an apparatus or system that includes a computing device such as the computing device in FIG. 6.

FIG. 7 is a flow diagram illustrating an example method to image a treatment area using a time gated image capture component and electronic display that may be performed by an apparatus or system that includes a computing device such as the computing device in FIG. 6, arranged in accordance with at least some embodiments described herein.

Example methods may include one or more operations, functions or actions as illustrated by one or more of blocks 722, 724, 726, and 728, and may in some embodiments be performed by a computing device such as the computing device 710 in FIG. 7. Such operations, functions, or actions in FIG. 7 and in the other figures, in some embodiments, may be combined, eliminated, modified, and/or supplemented with other operations, functions or actions, and need not necessarily be performed in the exact sequence as shown. The operations described in the blocks 722, 724, 726, and 728 may also be implemented through execution of computer-executable instructions stored in a computer-readable medium such as a computer-readable medium 720 of a computing device 710.

An example process to image a treatment area using a time gated image capture component and electronic display may begin with block 722, "DIRECT LASER PULSES TOWARDS A TREATMENT AREA OF AN EYE", where one or more laser pulses are directed toward the treatment area of an eye undergoing laser treatment. The laser pulses may be emitted by a laser source under the control of a laser controller. The laser controller may transmit the timing of the one or more laser pulses to a gating component.

Block 722 may be followed by block 724, "GENERATE IMAGE DATA RELATED TO THE TREATMENT AREA BY DETECTING LIGHT REFLECTED FROM AN AREA THAT INCLUDES THE TREATMENT AREA", where light reflected from the area that includes treatment area may be detected by one or more image capture components. For example, an image capture component may be a camera capable of detecting light in one or more spectral ranges which may include a visible light range, an ultra-violet (UV) light range, an infrared (IR) light range, and/or a sub-spectral range. The one or more image capture components may convert the detected light to a signal, may generate image data based on the signal. The one or more image capture components may also perform operations to enhance the image data such as edge filtering, edge detection, area agglomeration, contrast adjustment, or overlaying the image data to highlight changes in the treatment area among other techniques.

Block 724 may be followed by block 726, "CONTROL THE GENERATION OF THE IMAGE DATA TO EXCLUDE LIGHT REFLECTED FROM THE AREA THAT INCLUDES THE TREATMENT AREA DURING A TIME PERIOD IN WHICH THE LASER PULSES ARE INCIDENT ON THE TREATMENT AREA", where the gating component may transmit instructions to the one or more image capture devices based on a time period the one or more laser pulses are incident on the treatment area. The gating component may determine the time period by determining the timing of laser pulses directed toward the treatment area, determining the duration of the laser pulses, and/or determining a time interval between the laser pulses. The gating component may also determine the time period by determining an intensity associated with the light reflected from the area that includes treatment area, inferring one or more laser pulses are incident on the treatment area based on the intensity being above a particular threshold, and determining the time period based on the duration the intensity is above the threshold. Example instructions may include instructing the one or more image capture devices to cease detection during the time period or instructing the one or more image capture devices to exclude light detected during the time period from the generated image data. The gating component may also instruct the one or more image capture components to exclude image data from the time period when providing the image data for display or may transmit instructions to the one or more image capture devices to close the optical shutter during the time period.

Block 726 may be followed by block 728, "PROVIDE THE IMAGE DATA TO BE DISPLAYED ON AN ELECTRONIC DISPLAY TO PRESENT AN IMAGE OF THE TREATMENT AREA DURING THE LASER TREATMENT", where the one or more image capture components may provide the image data to be displayed on an electronic display. The electronic display may be integrated with a laser treatment system, integrated with the one or more image capture components, or may be a separate display device such as a computer monitor, a television, a projector, a mobile device, or a stereoscopic display device for example. The electronic display may have one or more user interface components such as menus, controller elements, or overlays.

The operations included in process 700 are for illustration purposes. Imaging a treatment area using a time gated image capture component and electronic display may be implemented by similar processes with fewer or additional operations, as well as in different order of operations using the principles described herein. The operations described herein may be executed by one or more processors operated on one or more computing devices, one or more processor cores, specialized processing devices, and/or general purpose processors, among other examples.

Figure 8:
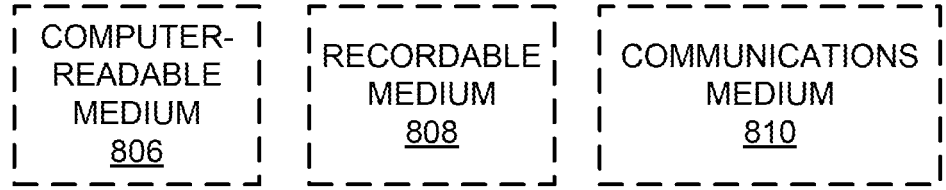
FIG. 8 illustrates a block diagram of an example computer program product.

FIG. 8 illustrates a block diagram of an example computer program product, some of which are arranged in accordance with at least some embodiments described herein.

In some examples, as shown in FIG. 8, a computer program product 800 may include a signal bearing medium 802 that may also include one or more machine readable instructions 804 that, in response to execution by, for example, a processor may provide the functionality described herein. Thus, for example, referring to the processor 604 in FIG. 6, the controller 622 may perform or control performance of one or more of the tasks shown in FIG. 8 in response to the instructions 804 conveyed to the processor 604 by the signal bearing medium 802 to perform actions associated with imaging a treatment area using a time gated image capture component and electronic display as described herein. Some of those instructions 804 may include, for example, one or more instructions to direct laser pulses towards the treatment area of the eye, generate image data related to the treatment area by detecting light reflected from an area that includes treatment area, control the generation of the image data to exclude light reflected from the area that includes treatment area during a time period in which the laser pulses are incident on the treatment area, and provide the image data to be displayed on an electronic display to present an image of the treatment area during the laser treatment according to some embodiments described herein.

In some implementations, the signal bearing medium 802 depicted in FIG. 8 may encompass computer-readable medium 806, such as, but not limited to, a hard disk drive (HDD), a solid state drive (SSD), a compact disc (CD), a digital versatile disk (DVD), a digital tape, memory, etc. In some implementations, the signal bearing medium 802 may encompass recordable medium 808, such as, but not limited to, memory, read/write (R/W) CDs, R/W DVDs, etc. In some implementations, the signal bearing medium 802 may encompass communications medium 810, such as, but not limited to, a digital and/or an analog communication medium (e.g., a fiber optic cable, a waveguide, a wired communication link, a wireless communication link, etc.). Thus, for example, the computer program product 800 may be conveyed to one or more modules of the processor 604 by an RF signal bearing medium, where the signal bearing medium 802 is conveyed by the communications medium 810 (e.g., a wireless communications medium conforming with the IEEE 802.11 standard).

According to some examples, a method of imaging a treatment area of an eye undergoing laser treatment may comprise directing laser pulses towards the treatment area of the eye, generating image data related to the treatment area by detecting light reflected from an area that includes treatment area, controlling the generation of the image data to exclude light reflected from the area that includes treatment area during a time period in which the laser pulses are incident on the treatment area, and providing the image data to be displayed on an electronic display to present an image of the treatment area during the laser treatment.

In other examples, controlling the generation of the image data may comprise time-gating the generation of the image data to exclude the light reflected from the area that includes treatment area during the time period in which the laser pulses are incident on the treatment area. In further examples, time-gating the generation of the image may comprise preventing the detection of the light reflected from the area that includes treatment area during the time period in which the laser pulses are incident on the treatment area. According to some examples, the detected light reflected from the area that includes treatment area may be converted to a signal, and time-gating the generation of the image may comprise excluding a portion of the signal corresponding to the light reflected during the time period in which the laser pulses are incident on the treatment area. In some examples, the image data may be generated based on the signal, and time-gating the generation of the image may comprise excluding a portion of the image data corresponding to the time period in which the laser pulses are incident on the treatment area. In further examples, the method may further comprise monitoring the portion of the signal excluded or the portion of the image data excluded to evaluate an operation of the direction of the laser pulses towards the treatment area of the eye.

In other examples, the method may further comprise determining the time period in which the laser pulses are incident on the treatment area. According to further examples, determining the time period may comprise determining an intensity associated with the light reflected from the area that includes treatment area, inferring the laser pulses are incident on the treatment area responsive to a determination that the intensity is above a particular threshold, and determining the time period based on a duration for which the intensity is determined to be above the particular threshold. In some examples, determining the time period may comprise determining a timing of the laser pulses, which may comprise determining a duration of each of the laser pulses. In further examples, determining the timing of the laser pulses may comprise determining a time interval in between each of the laser pulses.

According to some embodiments, an apparatus provided for imaging a treatment area of an eye undergoing laser treatment may comprise a treatment system that may be configured to direct laser pulses towards the treatment area of the eye and an imaging system comprising at least one image capture component. The imaging system may be configured to detect light reflected from an area that includes treatment area, generate image data related to the treatment area based on the light reflected from the area that includes treatment area, and provide the image data to be displayed on an electronic display to present an image of the treatment area during the laser treatment. Generation of the image data may be time-gated to exclude light reflected from the area that includes treatment area during a time period in which the laser pulses directed by the treatment system are incident on the treatment area. The apparatus may also comprise a controller communicatively coupled to the image capture component that may be configured to control performance of operations by the image capture component.

In other embodiments, the treatment system may comprise a laser source configured to generate the laser pulses and one or more optical elements configured to direct the laser pulses towards the treatment area of the eye. According to other embodiments, where the image capture component may comprise a lens configured to receive the light reflected from the area that includes treatment area an image sensor configured to detect and convert the light reflected from the area that includes treatment area to a signal, and an image processor configured to generate the image data based on the signal. In further embodiments, the image capture component may be a camera and may further comprise an optical shutter.

In some embodiments, in order to time-gate the generation of the image data, the controller may be configured to instruct the optical shutter to activate in order to block the image sensor during the time period in which the laser pulses are incident on the treatment area. In other embodiments, in order to time-gate the generation of the image data, the controller may be configured to instruct the image sensor to exclude a portion of the signal corresponding to the light reflected during the time period in which the laser pulses are incident on the treatment area. In further embodiments, in order to time-gate the generation of the image data, the controller may be configured to instruct the image processor to exclude a portion of the image data corresponding to the time period in which the laser pulses are incident on the treatment area.

In further embodiments, the controller may be further configured to determine the time period in which the laser pulses are incident on the treatment area. According to some embodiments, in order to determine the time period, the controller may be configured to determine an intensity associated with the light reflected from the area that includes treatment area, infer the laser pulses are incident on the treatment area responsive to a determination that the intensity is above a particular threshold, and determine the time period based on a duration for which the intensity is determined to be above the particular threshold. In other embodiments, in order to determine the time period, the controller may be configured to determine a timing of the laser pulses based on one or more of a duration of each of the laser pulses and a time interval in between each of the laser pulses.

In other embodiments, the treatment system may comprise a laser controller, and the laser controller may be configured to control the direction of the laser pulses towards the treatment area of the eye and provide the timing of the laser pulses to the controller. In some embodiments, the imaging system may comprise two or more image capture components. In further embodiments, a first image capture component may be configured to generate a first set of image data and a second image capture component may be configured to generate a second set of image data such that the first set of image data and the second set of image data may be provided to be displayed on the electronic display to present a stereoscopic image of the treatment area during the laser treatment. According to some embodiments, the two or more image capture components may be capable of detecting light in one or more spectral ranges, which may include a visible light range, an ultra-violet (UV) light range, an infrared (IR) light range, or a sub-spectral range, and may have a distinct light level setting.

In some embodiments, the image data may comprise one or more images which may be a sequence of images. In other embodiments, the electronic display may be integrated with the imaging system or may be a separate display device. In further embodiments, the electronic display may be integrated with a display system communicatively coupled to the imaging system. In some embodiments, the display system may comprise a user interface configured to enable interaction with the image data displayed on the electronic display.

According to other examples, an imaging system for imaging a target area undergoing laser treatment may comprise a lens that may be configured to receive light reflected from the target area in response to laser pulses being directed towards the target area by a laser source communicatively coupled to the imaging system, an image sensor that may be configured to detect and convert the light reflected from the target area to a signal, and an image processor. The image processor may be configured to generate image data based on the signal and provide the image data to be displayed on an electronic display to present an image of the target area during the laser treatment. The imaging system may further comprise a gating component that may be configured to control a time-gating of the imaging system such that the image data excludes light reflected from the target area during a time period in which the laser pulses directed by the laser source are incident on the target area.

In some examples, the imaging system may further comprise an optical shutter, and the gating component may be configured to instruct the optical shutter to activate in order to block the image sensor during the time period in which the laser pulses are incident on the target area. In other examples, the gating component may be configured to instruct the image sensor to exclude a portion of the signal corresponding to the time period in which the laser pulses are incident on the target area. According to some examples, the gating component may be configured to instruct the image processor to exclude a portion of the image data corresponding to the time period in which the laser pulses are incident on the target area.

In further examples, the gating component may be configured to determine the time period in which the laser pulses are incident on the target area. In some examples, in order to determine the time period, the gating component may be configured to determine an intensity associated with the light reflected from the target area, infer the laser pulses are incident on the target area responsive to a determination that the intensity is above a particular threshold, and determine the time period based on a duration for which the intensity is determined to be above the particular threshold. According to other examples, in order to determine the time period, the gating component may be configured to determine a timing of the laser pulses based on one or more of a duration of each of the laser pulses and a time interval in between each of the laser pulses. In some examples, the gating component may be configured to receive the timing of the laser pulses from a laser controller associated with the laser source. The laser controller may be configured to control the laser pulses directed by the laser source towards the target area of the eye.

In other examples, the lens, the image sensor, and the image processor may be integrated in an image capture component of the imaging system. According to some examples, the imaging system may comprise two or more image capture components, and the image capture component may be a camera. In further examples, a first image capture component may be configured to generate a first set of image data and a second image capture component may be configured to generate a second set of image data such that the first set of image data and the second set of image data may be provided to be displayed on the electronic display to present a stereoscopic image of the target area during the laser treatment.

In some examples, the two or more image capture components may be capable of detecting light in one or more spectral ranges, and the one or more spectral ranges may include a visible light range, an ultra-violet (UV) light range, an infrared (IR) light range, and/or a sub-spectral range. In other examples, the two or more image capture components may have a distinct light level setting. In further examples, the image sensor may include a charged coupled device (CCD), a complementary metal-oxide-semiconductor (CMOS), or a N-type metal-oxide-semiconductor (NMOS). According to some examples, the electronic display may be one of: integrated with the imaging system, integrated with a display system communicatively coupled to the imaging system, or a separate device. In other examples, the target area may be a treatment area of an eye.

There are various vehicles by which processes and/or systems and/or other technologies described herein may be effected (e.g., hardware, software, and/or firmware), and the preferred vehicle will vary with the context in which the processes and/or systems and/or other technologies are deployed. For example, if an implementer determines that speed and accuracy are paramount, the implementer may opt for mainly hardware and/or firmware vehicle; if flexibility is paramount, the implementer may opt for mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, each function and/or operation within such block diagrams, flowcharts, or examples may be implemented, individually and/or collectively, by a wide range of hardware, software, firmware, or virtually any combination thereof. In one embodiment, several portions of the subject matter described herein may be implemented via application specific integrated circuits (ASICs), field programmable gate arrays (FPGAs), digital signal processors (DSPs), or other integrated formats. However, some aspects of the embodiments disclosed herein, in whole or in part, may be equivalently implemented in integrated circuits, as one or more computer programs executing on one or more computers (e.g., as one or more programs executing on one or more computer systems), as one or more programs executing on one or more processors (e.g., as one or more programs executing on one or more microprocessors), as firmware, or as virtually any combination thereof, and designing the circuitry and/or writing the code for the software and/or firmware would be possible in light of this disclosure.

The present disclosure is not to be limited in terms of the particular embodiments described in this application, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of the appended claims. The present disclosure is to be limited only by the terms of the appended claims, along with the full scope of equivalents to which such claims are entitled. The terminology used herein is for the purpose of describing particular embodiments only, and is not intended to be limiting.

In addition, the mechanisms of the subject matter described herein are capable of being distributed as a program product in a variety of forms, and an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive (HDD), a compact disc (CD), a digital versatile disk (DVD), a digital tape, a computer memory, a solid state drive (SSD), etc.; and a transmission type medium such as a digital and/or an analog communication medium (e.g., a fiber optic cable, a waveguide, a wired communication link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein may be integrated into a data processing system via a reasonable amount of experimentation. A data processing system may include one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors.

A data processing system may be implemented utilizing any suitable commercially available components, such as those found in data computing/communication and/or network computing/communication systems. The herein described subject matter sometimes illustrates different components contained within, or connected with, different other components. Such depicted architectures are merely exemplary, and in fact, many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically connectable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). If a specific number of an introduced claim recitation is intended, such an intent will be explicitly recited in the claim, and in the absence of such recitation no, such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

For any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments are possible. The various aspects and embodiments disclosed herein are for purposes of illustration and are not intended to be limiting, with the true scope and spirit being indicated by the following claims.

What is claimed is:

1. An apparatus provided for imaging a treatment area of an eye undergoing laser treatment, the apparatus comprising:
    a treatment system configured to direct one or more laser pulses towards the treatment area of the eye;
    an imaging system comprising at least one image capture component configured to:
    detect light reflected from an area that includes the treatment area;
    generate image data related to the treatment area based on the light reflected from the area that includes the treatment area, wherein generation of the image data is time-gated to exclude light reflected from the area that includes the treatment area during a time period in which the one or more laser pulses directed by the treatment system are incident on the treatment area; and
    provide the image data to be displayed on an electronic display to present an image of the treatment area during the laser treatment; and
    a controller communicatively coupled to the image capture component, the controller configured to control performance of operations by the image capture component based on a comparison of an intensity of the light reflected from the area with a particular threshold.

2. The apparatus of claim 1, wherein the treatment system comprises a laser source configured to generate the one or more laser pulses and one or more optical elements configured to direct the one or more laser pulses towards the treatment area of the eye.

3. The apparatus of claim 1, wherein the image capture component comprises:
    a lens configured to receive the light reflected from the area that includes the treatment area;
    an image sensor configured to detect and convert the light reflected from the area that includes the treatment area to a signal; and
    an image processor configured to generate the image data based on the signal.

4. The apparatus of claim 3, wherein, to time-gate the generation of the image data, the controller is configured to:
    instruct the image sensor to exclude a portion of the signal corresponding to the light reflected during the time period in which the one or more laser pulses are incident on the treatment area; or
    instruct the image processor to exclude a portion of the image data corresponding to the time period in which the one or more laser pulses are incident on the treatment area.

5. The apparatus of claim 1, wherein
    the image capture component further comprises an optical shutter, and to time-gate the generation of the image data, the controller is configured to instruct the optical shutter to activate in order to block the image sensor during the time period in which the one or more laser pulses are incident on the treatment area.

6. The apparatus of claim 1, wherein the controller is further configured to:
   determine the intensity associated with the light reflected from the area that includes the treatment area;
   infer the one or more laser pulses are incident on the treatment area when the intensity is above the particular threshold; and
   determine the time period in which the one or more laser pulses directed by the treatment system are incident on the treatment area based on a duration for which the intensity is above the particular threshold.

7. The apparatus of claim 6, wherein the treatment system comprises a laser controller, and the laser controller is configured to:
   control a direction of the one or more laser pulses towards the treatment area of the eye; and
   provide a timing of the one or more laser pulses to the controller to determine the time period in which the one or more laser pulses directed by the treatment system are incident on the treatment area.

8. The apparatus of claim 1, wherein the imaging system comprises a first image capture component is configured to generate a first set of image data and a second image capture component configured to generate a second set of image data such that the first set of image data and the second set of image data are provided to be displayed on the electronic display to present a stereoscopic image of the treatment area during the laser treatment.

9. The apparatus of claim 8, wherein the first and second image capture components are capable of detecting light in one or more spectral ranges, the one or more spectral ranges including a visible light range, an ultra-violet (UV) light range, an infrared (IR) light range, or a sub-spectral range.

10. The apparatus of claim 1, further comprising a contact lens configured to be disposed on a surface of the eye and direct the one or more laser pulses toward the treatment area in the eye.

11. An imaging system for imaging a target area of an eye undergoing laser treatment, the imaging system comprising:
   a lens configured to receive light reflected from the target area in response to one or more laser pulses being directed towards the target area by a laser source communicatively coupled to the imaging system;
   an image sensor configured to detect and convert the light reflected from the target area to a signal;
   an image processor configured to:
      generate image data based on the signal;
      provide the image data to be displayed on an electronic display to present an image of the target area during the laser treatment; and
   a gating component configured to determine a time period in which the one or more laser pulses directed by the laser source are incident on the target area based on a comparison of an intensity of the light reflected from the target area with a particular threshold and control a time-gating of the imaging system such that the image data excludes light reflected from the target area during the time period.

12. The imaging system of claim 11, wherein the imaging system further comprises an optical shutter, and the gating component is configured to instruct the optical shutter to activate in order to block the image sensor during the time period in which the one or more laser pulses are incident on the target area.

13. The imaging system of claim 11, wherein the gating component is configured to instruct the image sensor to exclude:
   a portion of the signal corresponding to the time period in which the one or more laser pulses are incident on the target area, or
   a portion of the image data corresponding to the time period in which the one or more laser pulses are incident on the target area.

14. The imaging system of claim 11, wherein, to determine the time period in which the one or more laser pulses are incident on the target area, the gating component is configured to determine a timing of the one or more laser pulses based on one or more of a duration of each of the one or more laser pulses and a time interval in between each of the laser pulses.

15. The imaging system of claim 14, wherein the gating component is configured to receive the timing of the one or more laser pulses from a laser controller associated with the laser source, the laser controller configured to control the one or more laser pulses directed by the laser source towards the target area of the eye.

* * * * *